United States Patent
Ito et al.

[11] Patent Number: 5,804,142
[45] Date of Patent: Sep. 8, 1998

[54] CHROMATOGRAPH SYSTEM AND METHOD FOR MAINTAINING SYSTEM SUITABILITY THEREOF

[75] Inventors: Masahito Ito; Junkichi Miura; Yoshio Fujii; Hiroshi Satake, all of Katsuta; Kasumi Yoshida, Mito, all of Japan

[73] Assignee: Hitachi, Ltd., Tokyo, Japan

[21] Appl. No.: 756,430

[22] Filed: Nov. 26, 1996

Related U.S. Application Data

[62] Division of Ser. No. 364,440, Dec. 27, 1994, abandoned, which is a continuation of Ser. No. 149,701, Nov. 9, 1993, abandoned, which is a continuation of Ser. No. 763,203, Sep. 20, 1991, abandoned.

[30] Foreign Application Priority Data

Sep. 21, 1990 [JP] Japan ..................... 2-252302

[51] Int. Cl.$^6$ .................................................. G01N 30/02
[52] U.S. Cl. ..................... 422/70; 73/23.36; 73/61.57; 210/198.2; 364/497; 422/89; 436/161
[58] Field of Search ............... 422/68.1, 70, 89; 436/161, 66, 93; 210/656, 198.2; 73/61.52, 61.57, 23.22, 23.36; 364/497, 498

[56] References Cited

U.S. PATENT DOCUMENTS

| | | | |
|---|---|---|---|
| 4,108,603 | 8/1978 | Regnier et al. | 436/66 |
| 4,600,696 | 7/1986 | Solomons | 436/161 |
| 4,650,499 | 3/1987 | Scott | 422/89 |
| 4,674,323 | 6/1987 | Rulf et al. | 73/61.52 |
| 4,719,017 | 1/1988 | Uchino | 55/67 |
| 4,802,981 | 2/1989 | Kenney et al. | 210/198.2 |
| 4,810,391 | 3/1989 | Bruegger | 436/161 |
| 4,969,993 | 11/1990 | Nash, Jr. et al. | 73/61.52 |
| 5,039,409 | 8/1991 | Blaffert | 73/61.52 |
| 5,093,267 | 3/1992 | Miura et al. | 210/198.2 |

FOREIGN PATENT DOCUMENTS

| | | |
|---|---|---|
| 49-123398 | 11/1974 | Japan . |
| 61-25058 | 2/1986 | Japan . |
| 62-58168 | 3/1987 | Japan . |

OTHER PUBLICATIONS

American Laboratory, Feb. 1990, Cole, Alun "An instrumental response to confidence in LC analysis".
Dolan, John W., Troubleshooting LC Systems, The Humean Press, Inc., Clifton, NJ 1909. pp. 18, 22–24.

*Primary Examiner*—Jan Ludlow
*Attorney, Agent, or Firm*—Antonelli, Terry, Stout & Kraus, LLP

[57] ABSTRACT

A reference sample having a known concentration is injected into a chromatograph system before an unknown sample is analyzed. This is for the purpose of checking the deterioration of system performance or in other words for the purpose of checking system suitability. In the present invention, the chromatographic characteristic of the check sample at the time of deterioration of the system suitability is expected and stored in a memory in advance to be related to factors of deterioration of system suitability. A factor of deterioration is deduced by comparison between the actually analyzed chromatographic characteristic of the check sample and the relational data stored in the memory. A guidance required for removing the factor is displayed. Disclosed are preferred embodiments of a chromatograph system suitable for analyzing catecholamine or glycated hemoglobin.

25 Claims, 5 Drawing Sheets

CHROMATOGRAPH SYSTEM AND METHOD FOR MAINTAINING SYSTEM SUITABILITY THEREOF

This application is a Divisional application of application Ser. No. 08/364,440, filed Dec. 27, 1994, now abandoned which is a Continuation of application Ser. No. 08/149,701, filed Nov. 9, 1993, now abandoned which is a Continuation of application Ser. No. 07/763,203, filed Sep. 20, 1991 now abandoned.

BACKGROUND OF THE INVENTION

The present invention relates to a chromatograph system and a method for improving the system suitability thereof. In particular, it relates to a system and a method useful for maintaining the system suitability.

Heretofore, a technique for diagnosing deterioration of the sensitivity (or characteristic) of a chromatograph system by comparison between a component concentration as a chromatogram obtained by analyzing a standard (reference) sample having a known component concentration and a given component concentration has been proposed in the field of chromatograph, as disclosed in Japanese Patent Unexamined Publication Nos. Sho-55-160849 and Sho-56-6158. In the case where the chromatogram of the sample is corrected on the basis of the diagnostic data or in the case where the chromatogram is very abnormal, an alarm or the like is given to an operator to inform him/her of deterioration of system suitability.

In Japanese Patent Unexamined Publication No. Sho. 56-90259, the rate A/H of peak area A to peak height H is used to make a judgment by the same deviation from the preliminarily stored rate As/Hs in the standard sample. Here, As and Hs respectively represent the peak area and peak height of the standard sample.

On the other hand, a chromatograph system in which various types of information can be given to the operator during sample analysis is known (see Alun Cole, American Laboratory).

SUMMARY OF THE INVENTION

An object of the present invention is to provide a system and a method for easily maintaining the system suitability of a chromatograph system excellent in operating properties for execusive use for analyzing a specific sample.

Such an exclusive-use system is on high demand, because the system can be easily operated by an unskilled operator.

In general, in the chromatograph system, characteristics of stationary phases (columns, etc.), mobile phases (eluents, etc.), reference samples and the like are deteriorated as analyses are repeated. As a result, the chromatogram obtained contains error. In particular, when hormone in blood, etc. are analyzed for diagnoses of human diseases, a failure is not permitted because the amount of the sample is small. When the characteristics of the system are deteriorated, however, the chromatogram obtained is not reliable. Therefore, the characteristics of the system must be always maintained. Therefore, the aforementioned conventional techniques have been proposed.

When deterioration of the characteristics of the system is detected, it is a matter of course that the characteristics of the system must be recovered by some measure. It is, however, difficult to ask that the unskilled operator must make some measure.

Therefore, an object of the present invention is to provide a system and a method in which some measure to recover the characteristics of the system can be made easily by the unskilled operator. As a result, the system suitability of the chromatograph system can be maintained easily and, accordingly, analyzing efficiency can be improved.

To attain the foregoing objects, according to the present invention, the chromatographic characteristics of a reference sample or check sample injected before analyses of unknown samples and factors influencing the characteristics of the system are relationally stored in a memory in advance to check system suitability. Because the chromatograph system is an exclusive-use system, the relational data are stored in the memory by the system producer itself. A real factor influencing the characteristics of the system is deduced from the actually analyzed chromatographic characteristics of the reference sample by reference to the relational data stored in the memory. As a result, the characteristics of the system just before the analyses of unknown samples can be known. At the same time, a guidance corresponding to the factor is displayed.

If the influence of the deduced factor on the system can be neglected, the content of the guidance is empty. On the other hand, when the influence cannot be neglected, the contents of the guidance indicate a measure to be made by the operator as will be described in embodiments. That is, the guidance contains information useful for recovering the characteristics of the system or in other words for recovering system suitability.

If the factor can be neglected, an unknown sample is directly analyzed.

System suitability can be maintained easily by the aforementioned method while the unknown sample is analyzed, by using an inside reference sample.

Examples of the chromatographic characteristics are (1) a characteristic concerning peak size such as peak area and peak height, (2) a characteristic concerning column efficiency such as the number of theoretical plates, peak width, etc., (3) a characteristic concerning the value for identifying the peak such as peak retention time, capacity factor, and (4) a characteristic concerning relations between peaks such as retention time difference between peaks, separation rate in peaks, etc.

For example, abnormality in peak size is considered to be caused by the amount, concentration and purity of standard reagents, and error in reaction conditions, etc. in the case of the chromatograph containing error in the amount of the injected reference sample, error in the concentration of the sample and a reaction.

Abnormality in peak retention time is considered to be caused by the concentration and composition of eluents, the column temperature, etc.

The peak width at half maximum and the rate A/H of area A to height increases as the number of times of analyzing the sample increases or in other words as column efficiency decreases. The number of theoretical plates decreases as column efficiency decreases.

A difference in reaction efficiency between the respective peaks can be known on the basis of the rate of the peak area of a peak to the peak area of another peak in the case of the chromatograph containing error in the proportion of the sample and a reaction as unevaluated on the basis of one peak area. The quantities $t_2-t_1$, $t_2/t_1$, $(t_2-t_0)/(t_1-t_0)$, etc. concerning the respective retention time of two peaks can deduce a factor mainly influencing the error in the retention time from the aforementioned factors. Further, the quantities for expressing separation of two peaks can express column efficiency more sensitively than the aforementioned quantities for expressing column efficiency.

Further, the dynamic range (the upper and lower limits of the concentration) and the linear relation between the concentration and the output can be utilized for checking the condition of the detector and the reaction condition in the case where the chromatograph is provided with a reaction.

In the present invention, the relation between cause and result is automatically displayed through a guidance.

Further, the precision of the chromatogram obtained by the chromatograph system can be evaluated. The relative standard deviation or changing width of peak size, retention time, etc. can be utilized by analyzing the reference sample N times. The reproducibility of a two-dimensional graph such as a spectroscopic graph can be evaluated.

A graph of the detected strength vs. the concentration can be evaluated by analyzing several kinds of reference samples different in concentration in order to check the quantitative dynamic range.

DESCRIPTION OF THE PREFERRED EMBODIMENTS

Figure 1:
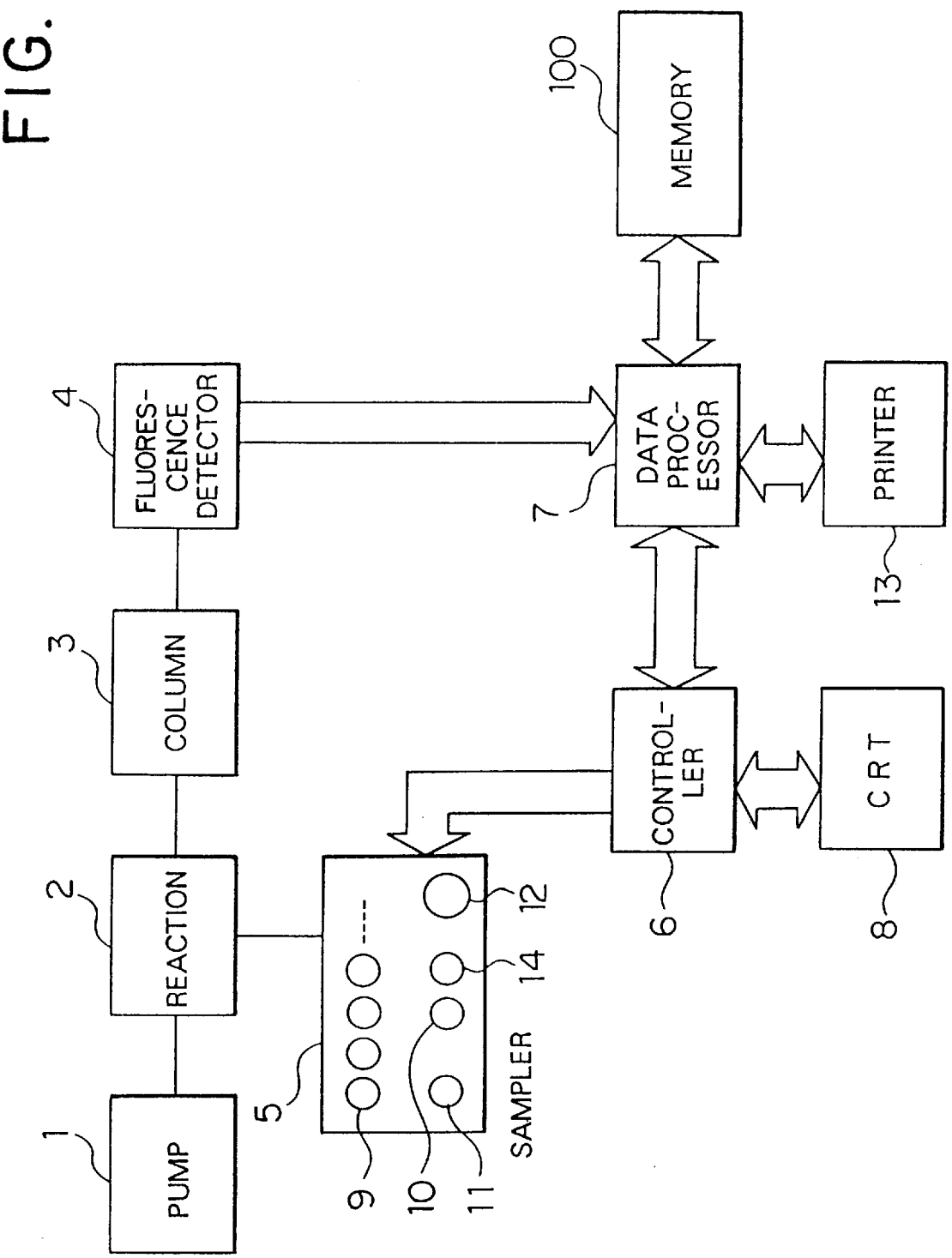
FIG. 1 is a system diagram of a catecholamine analyzer as a first embodiment of the present invention.

Referring to FIG. 1, a sample 5 having a nozzle freely movable in X, Y and Z directions sucks 400 $\mu$l of a reference sample 11 containing the three catecholamines of norepinephrine (NE), epinephrine (E) and dopamine (DA) in the amount of 500 pg/ml of each catecholamine and injects the reference sample into a mixing port 12.

Then, 400 $\mu$l of a fluorescent derivatizing reagent solution 10 of 60 mmol/l 1,2-diphenylethylenediamine is sucked and mixed with the reference sample 11 injected into the mixing port 12. Then, 400 $\mu$l of the mixture solution is delivered to a reaction section 2 to perform a fluorescent derivatizing reaction.

After two minutes, derivatized catecholamine is once sucked to a pre-column in the reaction section 2. After three minutes from that time, the derivatized catecholamine is delivered to a column 3 together with an eluent fed from a pump 1 by valve switching and is separated by reversed-phase chromatography, so that the derivatized catecholamine is finally detected by a fluorescence detector 4.

Figure 5:
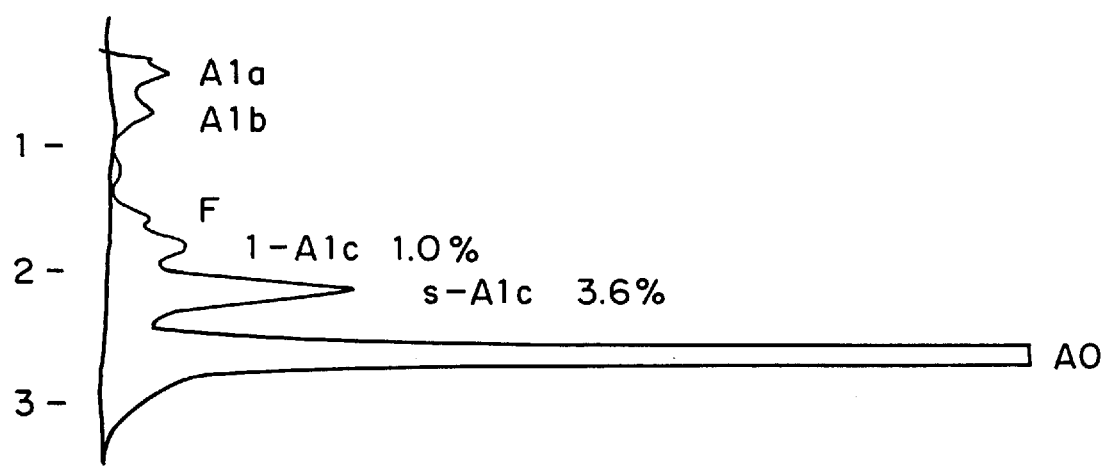
FIG. 5 is a chromatogram in glycated hemoglobin analysis.

An example of the chromatograph is shown in FIG. 5.

On the other hand, the relations between chromatographic characteristics of the reference sample and factors influencing the characteristic are stored in a memory 100. Describing more in detail, chromatographic characteristics at the time of occurrence of chromatographic abnormality caused by deterioration of system suitability and factors of deterioration of the system suitability are stored relationally. The relations are not individually stored in the memory 100 by operators but preliminarily stored in the memory 100 by the system producer, because this chromatograph system is provided as an exclusive-use system for analyzing catecholamine. Accordingly, this system can be easily used by the respective operators.

The characteristic of the chromatogram obtained by the fluorescence detector 4 is compared, in a data processing section 7, with the relation stored in the memory 100. In respect to the comparison, the data processing section 7 sends no data to a control section 6 if the characteristic of the chromatogram is not abnormal. In this case, no data is displayed on a printer 13 and a CRT 8. The flow of reference sample analysis has been described above.

In practice, the reference sample analysis is repeated three times. In the case where a decision is made that there is no abnormality in the three chromatograms, this result is reliable: a calibration is performed to plot a chromatogram on the printer 13 and to display the chromatogram on the CRT 8. It is considered that the chromatogram obtained by the three-times repetition of the reference sample analysis is more stable than the chromatogram obtained by once reference sample analysis, and there arises an advantage in that a reliable calibration can be performed. If there is no abnormality in the chromatogram, analyses of unknown samples 9 are successively performed in the same manner as in the reference sample 11.

Figure 2:
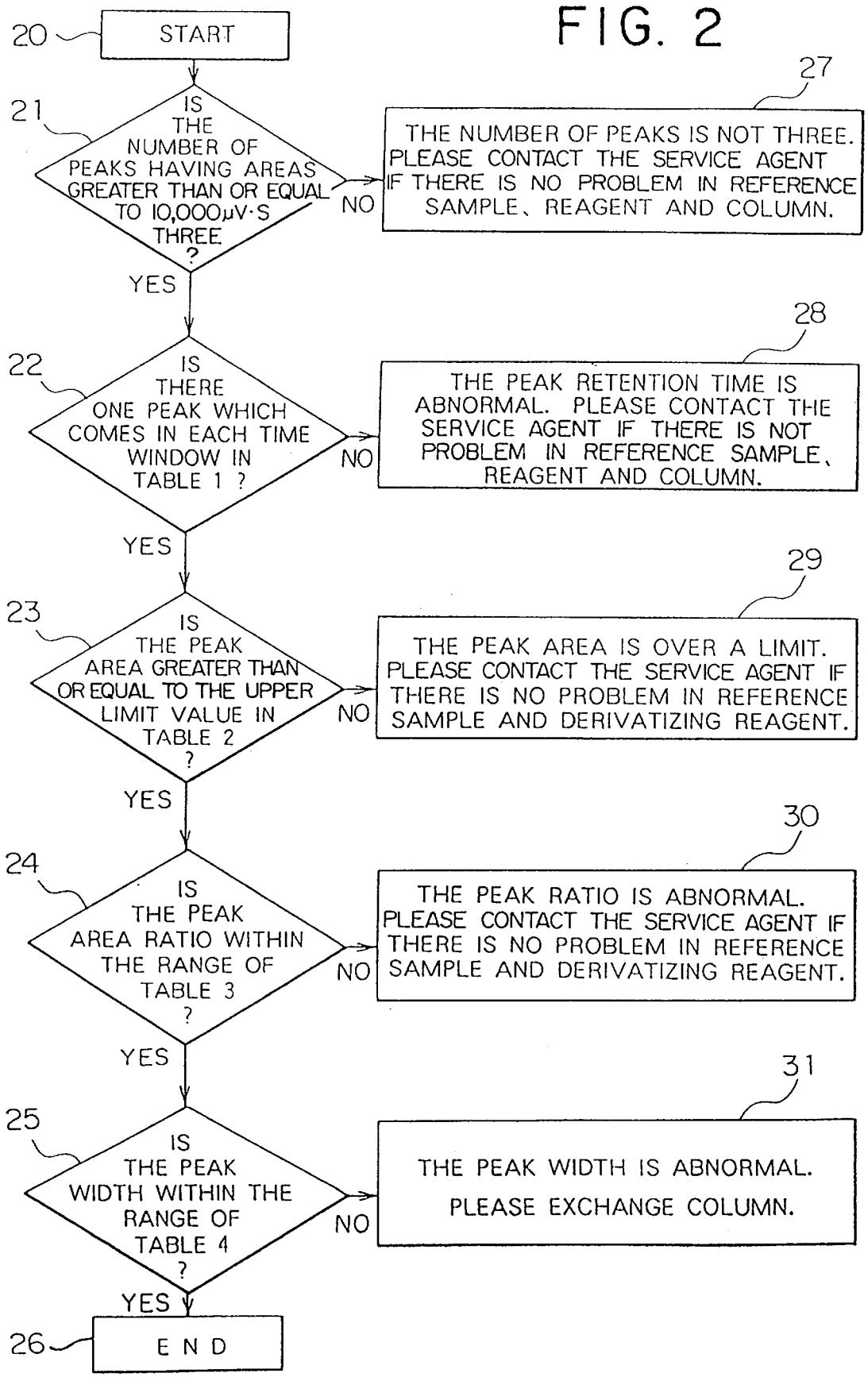
FIG. 2 is a flow chart of chromatogram diagnosis in the catecholamine analyzer.

A chromatogram assessment performed in the data processing section 7 will be described hereunder with reference to the flow chart of FIG. 2.

This routine is started from the diagnosis start 20. In the judgment 21, it is checked whether the peak areas of NE, E and DA are respectively larger than a lower-limit value (10,000 $\mu$V·s). When the number of peaks having larger peak areas than the lower-limit value is not larger than 2, several causes, such as shortage of the amount or concentration of the reference sample, shortage of the derivatizing reaction, or change in quality of the eluent to shift the retention time, are considered. When, on the contrary, the number of peaks is not smaller than 4, contamination of impurities into the reference sample, the derivatizing reagent or the flow path is considered. In any case, the data processing section 7 sends error to the control section 6 to prohibit progressing to analyses of unknown samples 9. The sampler 5 stops sampling and, at the same time, the control section 6 cleans both the sampler and the flow path to terminate the analysis. At this time, a guidance as shown in step 27 in FIG. 2 is displayed.

Another example of the guidance will be described hereunder.

When, for example, the number of peaks having larger areas than the lower-limit value is not smaller than 4, the following guidance is displayed: "Impurities in the reference sample may be considered as the cause that the number of peaks having larger areas than a limit is not smaller than 4. Exchange it for a new one, please. Contamination from reagents and deterioration of the pre-column may be considered as other causes." When, on the contrary, the number of peaks having larger areas than the lower-limit value is not larger than 2, the following guidance is displayed: "Deterioration of the reference sample or deterioration of reagents may be considered as the cause that the number of peaks having larger areas than a limit is smaller than 3. Exchange it for a new one, please. Deterioration of the column may be considered as another cause." When the number of peaks having larger areas than the lower-limit value is zero, the following guidance is displayed: "Use of an unsuitable reference sample or reagents may be considered as the cause that there is no peak having its larger area than a limit. Exchange it for a new one, please. Deterioration of the column may be considered as another cause."

Then, in the judgement 22, it is checked whether there is no shifting in the retention time. When the retention time of each peak is out of an allowed range, error is produced in the same manner as in the judgment 21, so that a guidance 28 is displayed. Change in quality of the eluent and deterioration of the column are considered as the main causes.

When the guidance 28 is displayed more specifically, the following guidance is displayed: "Deterioration of the eluent may be considered as the cause that the peak retention time is abnormal. Exchange it for a new one, please. Deterioration of reagents, deterioration of the reference sample and deterioration of the column may be considered as other causes."

TABLE 1

|    | Retention time (min) | ± Allowed range (min) |
|----|----------------------|------------------------|
| NE | 0.90                 | 0.10                   |
| E  | 1.20                 | 0.15                   |
| DA | 2.50                 | 1.00                   |

TABLE 2

|    | Upper-limit value ($\mu V \cdot s$) |
|----|--------------------------------------|
| NE | 1500000                              |
| E  | 1000000                              |
| DA | 525000                               |

TABLE 3

|       | AREA RATE | ± Allowed range |
|-------|-----------|-----------------|
| NE/E  | 1.250     | 0.250           |
| DA/E  | 0.625     | 0.100           |

TABLE 4

|    | A/H Upper limit (s) | A/H Lower limit (s) |
|----|---------------------|---------------------|
| NE | 10.0                | 0.5                 |
| E  | 20.0                | 0.5                 |
| DA | 25.0                | 0.5                 |

In the judgment 23, it is checked whether the peak area is not larger than an upper-limit value. When the peak area is larger than the upper-limit value as shown in Table 2, error is produced, so that a guidance 29 is displayed. Change in quality of the reference sample or the derivatizing reagent is considered as the main cause. When the guidance 29 is displayed more specifically, the following guidance is displayed: "Condensation of the reference sample or the derivatizing reagent may be considered as the cause that the peak area is larger than its upper-limit value. Exchange it for a new one, please."

In the judgment 24, it is checked whether each of the peak area rates (NE/E, DA/E) between components in the reference sample is in a predetermined range. When the peak area rate is out of the range as shown in Table 3, error is produced, so that a guidance 30 is displayed. Uneven progression of the derivatizing reaction in the respective catecholamine components may be considered as the main cause. When the guidance 30 is displayed more specifically, the following guidance is displayed: "Deterioration of the reference sample or the derivatizing reagent may be considered as the cause of abnormality of the peak area rate. Exchange it for a new one, please."

In the judgment 25, it is checked whether the peak width, that is, the rate A/H of the peak area A to the peak height H is in a range as shown in Table 4. When the peak width is out of the range shown in Table 4, error is produced, so that a guidance 31 is displayed. Deterioration of the column is considered as the main cause.

Finally, in the step 26, a series of judgment is terminated.

In the aforementioned embodiment, the situation of the routine does not go to the analyses of unknown samples 9 in the case where the chromatogram obtained by analyzing the reference sample 11 is abnormal. Although the embodiment has shown the case where shifting to the analyses of unknown samples 9 is prohibited simply, the invention can be applied to the case where shifting to the analyses of unknown samples 9 may be permitted at the point of time abnormality is lost through analyzing the reference sample 11 several times.

Because the reproducibility may be not attained in the first and second analyses in chromatography, a trial to repeat the analyzing of the reference sample 11 is effective.

Not only assessment of the system suitability by analyzing the reference sample 11 before analyzing unknown samples 9 but also assessment of the system suitability during the successive analyzing of unknown samples are effective, because the change in quality of the derivatizing reagent with the passage of time and the shifting of the retention time with the passage of time occur. For example, the reference sample 11 or a control sample is once analyzed whenever unknown samples 9 are analyzed five times in total. The chromatogram thus obtained is processed according to the algorithm shown in FIG. 2, to thereby assess system suitability. When abnormality is detected, sampling of the next unknown sample 9 is not performed so that the operator is informed of a guidance for a measure to remove a factor of abnormality.

Figure 4:
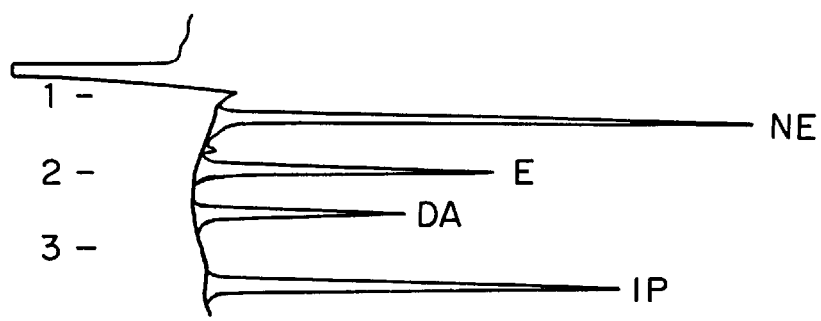
FIG. 4 is a chromatogram in catecholamine analysis.

An inside reference substance addition method can be used as another method for assessing system suitability on the way of analyzing of an unknown sample 9. This method is as follows. In the sample 5 as shown in FIG. 1, after a reference sample 11 or an unknown sample 9 is injected into the mixing port 12, 100 $\mu l$ of an inside reference substance 14 containing 500 pg/ml of isoproterenol (IP) is injected into the mixing port 12 and mixed. Then, a fluorescent derivatizing reagent solution 10 is mixed in the mixing port 12. When analyzing is performed in the same manner as described above, the peak of IP always having a predetermined retention time and a predetermined peak size appears in the chromatogram (FIG. 4). As described above, whenever the chromatogram of an unknown sample 9 is obtained, the area and retention time of IP can be compared with those obtained from the reference sample 11. In this case, it is not necessary to insert the analyzing of the reference sample 11 or control sample into the analyzing of the unknown sample 9. Accordingly, time saving is attained.

Figure 3:
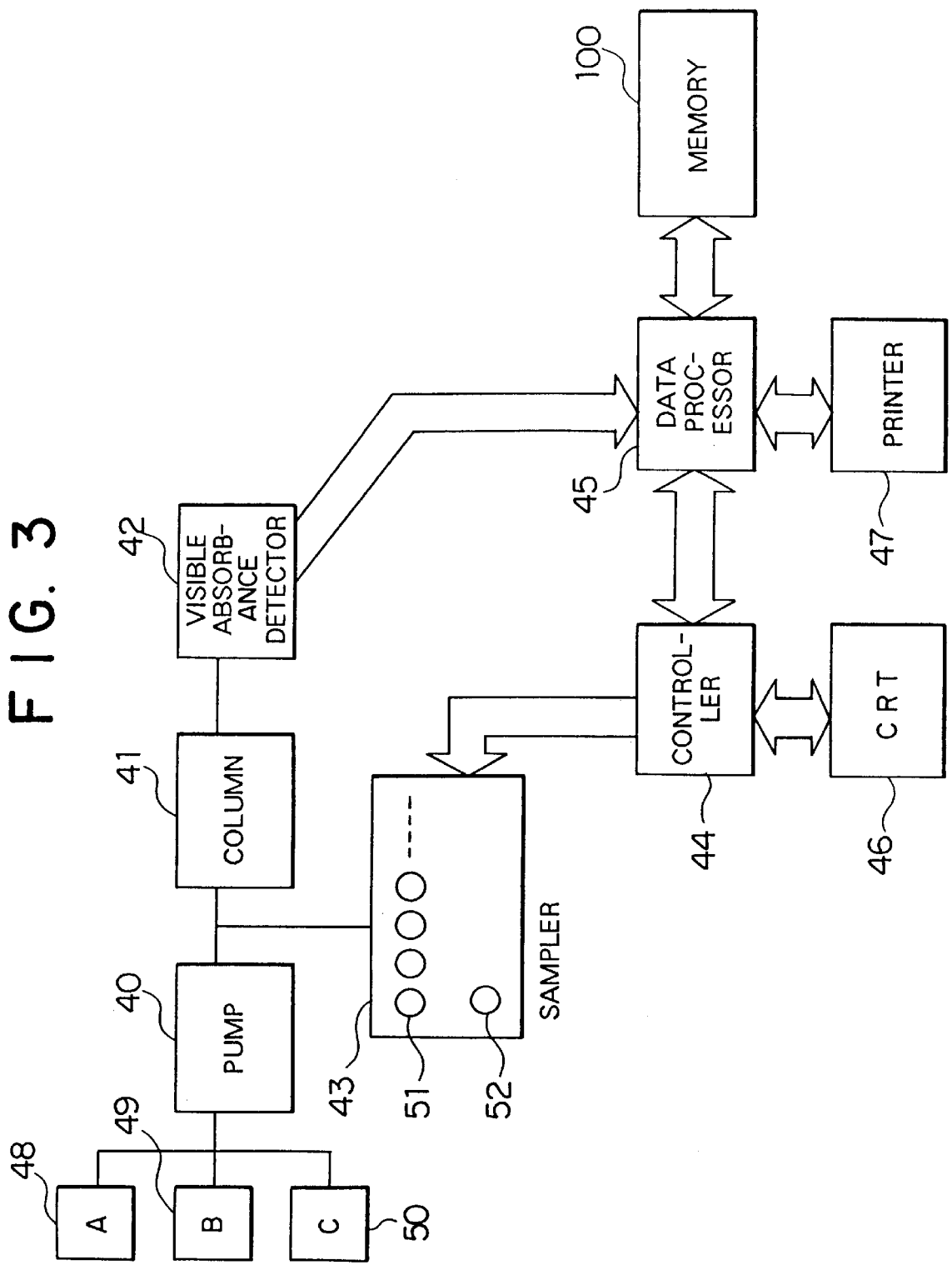
FIG. 3 is a system diagram of a glycated hemoglobin analyzer as a second embodiment of the present invention.

Another embodiment of the present invention will be described hereunder with reference to FIG. 3. FIG. 3 is a diagram of a liquid chromatograph system for ion-exchange chromatography for analyzing glycated hemoglobin.

A pump 40 feeds eluents A 48, B 49 and C 50 respectively for 1.9, 1.2 and 0.4 minutes in a cycle of 3.5 minutes by switching the eluents to perform stepwise elution. A sampler 43 sucks 10 $\mu l$ of a reference sample 52 of hemoglobin (Hb) and injects the reference sample into a flow path to a column 41. The reference sample 52 as a check sample is delivered to the column 41 together with the eluent A 48 and separated by ion-exchange chromatography. The reference sample 52 is further separated through the eluents B 49 and C 50 and finally detected by a visible absorbance detector 42. The chromatogram (FIG. 5) is processed in a data processing section 45 as will be described later.

If the chromatogram in the processing is in a normal range, a control section 44 gives an instruction to the sample 43 to such the reference sample 52 again.

The reason is as follows. In the ion-exchange chromatography, the eluents 48, 49 and 50 are switched in a cycle of 3.5 minutes, so that the next eluent is fed before the previous eluent is completely replaced by the current eluent in the column 41. In such circumstances, peak retention time may be unstable if the eluents are not switched for several cycles. To confirm the stability of retention time, in this embodiment, the reference sample 52 is analyzed two times to judge whether the retention time difference between the first and second peaks of s-Alc is not larger than 0.05 minutes. If the difference is not larger than 0.05 minutes, the situation of the routine goes to the analysis of an unknown sample 51. If the difference is larger than 0.05 minutes, the reference sample 11 is analyzed once more to judge whether the retention time difference between the second and third peaks of s-Alc is not larger than 0.05 minutes. If the difference is not larger than 0.05 minutes, the situation of the routine can go to the analysis of an unknown sample 51.

If the difference is larger than 0.05 minutes, a decision is made that the peak retention time is unstable and, at the same time, a guidance to get into communication with a service station is given to the operator through a CRT 46 or a printer 47.

The reproducibility of the chromatogram can be directly evaluated instead of the retention time difference. A coefficient of correlation is calculated on the basis of total or partial comparison between the first and second chromatograms. If the coefficient of correlation is not smaller than 0.999, the situation of the routine goes to the analysis of an unknown sample 51. At the same time, it is checked whether the inclination of the regression line is 1±0.01.

In practice, the peak retention time may be shifted by about 0.05 minutes with respect to the first retention time on the basis of the difference in the eluent switching time. Therefore, a method in which the second chromatogram is forcedly shifted at intervals of 0.01 minutes in a range of −0.05 minutes to +0.05 minutes with respect to the first chromatogram is effective when the coefficient of correlation is calculated by total or partial comparison between the first and second chromatograms. Eleven chromatograms shifted in a range of −0.05 minutes to +0.05 minutes can be generated, so that eleven coefficients of correlation can be calculated. When the maximum among the coefficients of correlation is not smaller than 0.999, the situation of the routine goes to the analysis of an unknown sample 51.

The technique of generating several chromatograms shifted at intervals of a time to calculate coefficients of correlation with respect to another chromatogram to thereby evaluate the reproducibility of the chromatogram in the maximum coefficient of correlation is effective for measuring the matching between the chromatogram obtained by analyzing the reference sample and a predetermined chromatogram.

Figure 6:
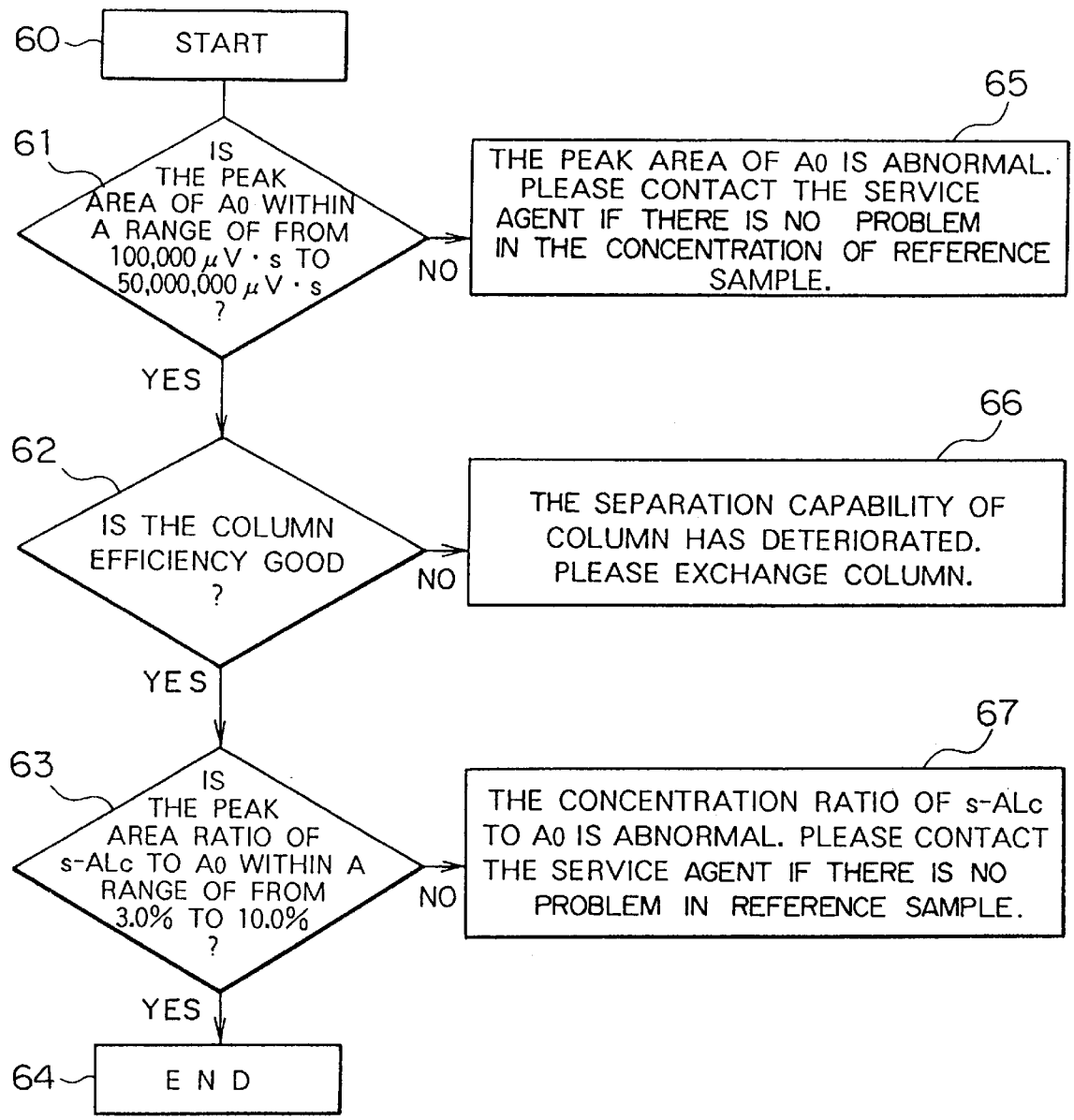
FIG. 6 is a flow chart of chromatogram diagnosis in the second embodiment.

Chromatogram diagnosis performed in the data processing section 45 will be described hereunder with reference to FIG. 6. Similarly to the first embodiment, chromatographic characteristics and factors are relationally stored in the memory 100.

The routine is started from the start 60. In the judgment 61, it is checked whether the peak area of hemoglobin $A_0$ is in a predetermined range.

When the peak area is not larger than 100,000 $\mu V \cdot s$, causes such as over-dilution of the reference sample 52, abnormality in injection from the sampler 43 to the flow path, abnormality in the detection section, etc., may be considered. When, on the contrary, the peak area is not smaller than 500,000,000 $\mu Vs$, causes, such as insufficient dilution of the reference sample 52, etc., may be considered. In any case, the data processing section 45 sends error to the control section 44. The control section 44 gives an instruction to the sampler 43 to stop sampling and cleans both the sampler and the flow path, so that the analyzing is terminated. At the same time, a guidance 65 concerning quality control is displayed on the CRT 46 or the printer 47.

Then, in the judgment 62, the column efficiency is evaluated. The number of the theoretical plates, the separation rate, the resolution, etc. can be used for evaluation of the column efficiency. In this embodiment, the three parameters of the peak area A, the peak height H and the retention time $t_R$ of $A_0$ are calculated to evaluate the column efficiency on the basis of the following formula:

$$t_R(\text{min}) \times H(\mu V)/A(\mu V \cdot s) \tag{1}$$

When the value of the formula (1) is not smaller than 0.10, a decision is made that column efficiency is good. The formula (1) is based on the fact that the number N of theoretical plates can be expressed by the following formula (2) on the assumption that the peak is Gaussian.

$$N = \left(\frac{tR}{\sigma}\right)^2 = 2\pi \left(\frac{tR \cdot H}{A}\right)^2 \tag{2}$$

In the formula, σ represents the Gaussian standard deviation.

In the case of the glycated hemoglobin analyzing system, there is no isocratic elution. Accordingly, the number of the theoretical plates is used for convenience. In practice, it is considered that the value obtained by calculating the following formula (3) on the consideration of time tc at which the eluent C 50 for elution of the peak of $A_0$ reaches the detector 42 is nearer to the meaning of the number of theoretical plates.

$$\{tR (\text{min}) - tc(\text{min})\} \times H(\mu V)/A(\mu V \cdot s) \tag{3}$$

When the value of the formula (1) is not smaller than 0.10, error is produced and a guidance 66 is displayed.

In the judgment 63, the ratio of the peak area of stable hemoglobin Alc (s-Alc) to $A_0$ is checked. The concentration of Alc in the reference sample is adjusted to be 6% with respect to the concentration of $A_0$. Accordingly, when the peak area ratio is out of the predetermined range, change in quality of the reference sample, error in peak identification, etc. may be considered. In this case, error is produced and a guidance 67 is displayed.

Finally, in the step 64, the routine is terminated.

Although the processing of the chromatogram of the reference sample 52 performed in the data processing section 45 has been described, the concentration of $A_0$, the peak area rate of s-Alc to $A_0$, etc. do not take extraordinary values in the case of glycated hemoglobin because the unknown sample 51 is whole blood or a dilution thereof. The flow chart of chromatogram diagnosis in FIG. 6 can be used for testing whether analysis is performed normally, by more or less modifying the predetermined range while the unknown sample 51 is analyzed. In the case of the unknown sample 51, the method is used for indicating that respective analyses are carried out normally, not for interrupting analyses.

When the catecholamine analyzing system in the first embodiment of the present invention is used for clinical testing, a subject obtained from a patient but never obtained again can be prevented from missing by the abnormality of the chromatograph system. Also in the case of measurement of samples obtained from experimental animals, precious subjects can be prevented from missing. If tens of unknown samples on the autosampler are subjected to analyses though the chromatogram of the reference sample is abnormal, not only consumption of the eluents and deterioration of the column are promoted but also the time required for the analyses is wasteful. In particular, wasteful consumption of the fluorescent derivatizing reagents has a large influence on cost. In the aforementioned embodiment, such circumstances can be prevented.

Because abnormality can be classified, the operator can be informed of the point to be corrected for normal analyses.

Also in the glycated hemoglobin analyzing system in the second embodiment of the invention, not only wasteful consumption of the eluents, deterioration of the column and wasteful consumption of the time required for analyses can be prevented but also the operator can be informed of a measure to abnormality.

As described above, according to the present invention, not only the abnormality of the chromatogram can be judged when the abnormality occurs in the chromatogram of a known sample such as a reference sample but also the operator can be informed of the point of the problem relationally to the quality control of fixed phases, movable phases, reagents, etc. used in the chromatograph. Accordingly, a measure thereto can be exactly given to the operator, so that an expert chromatograph system easy to use can be provided.

Although, the present invention has been described in detail, it should be understood that various changes, substitutions and alternations can be made hereto without departing from the spirit and scope of the present invention as defined by the appended claims.

What is claimed is:

1. A chromatograph system for analyzing a specific sample, comprising:

first storage means for storing a predetermined number indicative of a number of peaks of components to be detected;

second storage means for storing a reference retention time range;

analysis means for exclusively analyzing a predetermined check sample and a specific sample of interest to obtain chromatograms thereof;

means for comparing a number of peaks detected in the chromatograms of the check sample and the predetermined number, each detected peak being of a size greater than a predetermined lower-limit value;

means for inhibiting the specific sample of interest from being subjected to analysis by said analysis means and for informing an operator of a guidance indication that the check sample or a reagent may be deteriorated when the predetermined number and the detected number of peaks in the check sample chromatogram are not coincident;

first identification means for comparing the retention time of a predetermined peak in the chromatogram of the predetermined check sample and the reference retention time range when the predetermined number and the detected number of peaks in the check sample chromatogram are coincident;

first information means for informing an operator of a first guidance indication regarding an eluent when the retention time of the predetermined peak is out of the reference retention time range when the predetermined number and the detected number of peaks in the check sample chromatogram are coincident;

third storage means for storing a reference peak size range;

second identification means for comparing the peak size of the predetermined peak and the reference peak size range when the predetermined number and the detected number of peaks in the check sample chromatogram are coincident; and second information means for informing the operator of a second guidance indication regarding the predetermined check sample and a reagent being employed when the peak size of the predetermined peak is out of the reference peak size range when the predetermined number and the detected number of peaks in the check sample chromatogram are coincident.

2. A chromatograph system according to claim 1, further comprising means for automatically injecting an unknown sample into said analysis means when the retention time and the peak-size of the predetermined peak are both within the respective reference ranges.

3. A chromatograph system according to claim 2, further comprising:

further storage means for storing a reference peak size ratio range;

further identification means for comparing the peak size ratio of predetermined peaks in the chromatogram and the reference peak size ratio range when the peak size of the predetermined peak is within the reference peak size range; and further information means for informing the operator of a further guidance indication that directs the operator to check the predetermined check sample and the reagent when the peak size ratio of the predetermined peaks is out of the reference peak size ratio range.

4. A chromatograph system according to claim 1, wherein said first information means provides a first guidance indication that directs the operator to check the eluent, and said second information means provides a second guidance indication that directs the operator to check the predetermined check sample and the reagent.

5. A chromatograph system according to claim 4, further comprising:

fourth storage means for storing a reference peak width range;

third identification means for comparing the peak width of the predetermined peak and the reference peak width range when the predetermined number and the detected number of peaks in the check sample chromatogram are coincident; and third information means for informing the operator of a third guidance indication that directs the operator to exchange a separation column when the peak width of the predetermined peak is out of the reference peak width range when the predetermined number and the detected number of peaks in the check sample chromatogram are coincident.

6. A chromatograph system according to claim 1, wherein said analysis means comprises means for analyzing a biochemical sample obtained from a living body.

7. A chromatograph system according to claim 6, wherein said analysis means comprises means for analyzing a catecholamine or glycated hemoglobin.

8. A chromatograph system for analyzing a specific sample, comprising:

first storage means for storing a reference retention time range;

analysis means for exclusively analyzing a predetermined check sample and the specific sample of interest to obtain chromatograms thereof;

first identification means for comparing the retention time of a predetermined peak in the chromatogram of said predetermined check sample and the reference retention time range when a predetermined number and the detected number of peaks in the check sample chromatogram are coincident;

first information means for informing an operator of a first guidance indication regarding an eluent when the retention time of the predetermined peak is out of the reference retention time range when the predetermined number and the detected number of peaks in the check sample chromatogram are coincident;

second storage means for storing a reference peak size range;

second identification means for comparing the peak size of the predetermined peak and the reference peak size range when the predetermined number and the detected number of peaks in the check sample chromatogram are coincident;

second information means for informing the operator of a second guidance indication regarding the predetermined check sample being employed when the peak size of the predetermined peak is out of the reference peak size range when the predetermined number and the detected number of peaks in the check sample chromatogram are coincident;

third storage means for storing the predetermined number, indicative of a number of peaks of components to be detected;

means for comparing a number of peaks detected in the chromatograms of the check sample and said predetermined number, each detected peak being of a size greater than a predetermined lower-limit value; and means for inhibiting the specific sample of interest from being subjected to analysis by the analysis means and for informing an operator of a guidance indication that the check sample or a reagent may be deteriorated when the predetermined number and the detected number of peaks in the check sample chromatogram are not coincident.

9. A chromatograph system according to claim 8, wherein said first information means is also for informing the operator of a third guidance indication regarding a column when the retention time of the predetermined peak is out of the reference retention time range.

10. A chromatograph system according to claim 8, further comprising:

further storage means for storing a reference peak size ratio range;

further identification means for comparing the peak size ratio of predetermined peaks in the chromatogram and the reference peak size ratio range when the peak size of the predetermined peak is within the reference peak size range when the predetermined number and the detected number of peaks in the check sample chromatogram are coincident; and further information means for informing the operator of a further guidance indication that directs the operator to check the predetermined check sample when the peak size ratio of the predetermined peaks is out of the reference peak size ratio range when the predetermined number and the detected number of peaks in the check sample chromatogram are coincident.

11. A chromatograph system according to claim 8, further comprising:

further storage means for storing a reference peak size ratio range;

further identification means for comparing the peak size ratio of predetermined peaks in the chromatogram and the reference peak size ratio range when the peak size of the predetermined peak is within the reference peak size range when the predetermined number and the detected number of peaks in the check sample chromatogram are coincident; and further information means for informing the operator of a further guidance indication that directs the operator to check the predetermined check sample and the reagent when the peak size ratio of the predetermined peaks is out of the reference peak size ratio range when the predetermined number and the detected number of peaks in the check sample chromatogram are coincident.

12. A chromatograph system according to claim 8, further comprising:

fourth storage means for storing a reference peak width range;

third identification means for comparing the peak width of the predetermined peak and the reference peak width range when the predetermined number and the detected number of peaks in the check sample chromatogram are coincident; and further information means for informing the operator of a third guidance indication regarding a separation column when the peak width of the predetermined peak is out of the reference peak width range when the predetermined number and the detected number of peaks in the check sample chromatogram are coincident.

13. A chemical separation and detection system for analyzing a specific sample, comprising:

a separation column for separating a component of the sample, a detection means for detecting retention time, quantity and degree of separation of said component in the sample, first storage means for storing a reference retention time range for the component in a check sample, first identification means for comparing the reference retention time and a retention time of the component in the check sample when a predetermined number and the detected number of peaks in the check sample chromatogram are coincident, second storage means for storing a reference quantity of the component range in the check sample, second identification means for comparing the reference quantity of the component range and the quantity of the component in the check sample when the predetermined number and the detected number of peaks in the check sample chromatogram are coincident, first information means for informing an operator of a first guidance indication regarding an eluent when the retention time of the component in the check sample is out of the reference retention time range when the predetermined number and the detected number of peaks in the check sample chromatogram are coincident, second information means for informing the operator of a second guidance indication regarding the check sample and a reagent being employed when the quantity of a component in the check sample is out of the reference quantity of the component range when the predetermined number and the detected number of peaks in the check sample chromatogram are coincident, third storage means for storing the predetermined number indicative of a number of peaks of components to be detected, analysis means for exclusively analyzing the check sample and the specific sample of interest to obtain chromatograms thereof, means for comparing a number of peaks detected in the chromatograms of the check sample and said predetermined number, each detected peak being of a size greater than a predetermined lower-limit value, and means for inhibiting the specific sample of interest from being subjected to analysis by the analysis means and for informing an operator of a guidance indication that the check sample or a reagent may be deteriorated when the predetermined number and the detected number of peaks in the check sample chromatogram are not coincident.

14. A chemical separation and detection system according to claim 13, further comprising means for automatically injecting an unknown sample into said separation column when the retention time of the component and the quantity of the component in the check sample are both within respective reference ranges.

15. A chemical separation and detection system according to claim 13, wherein said first information means provides a first guidance indication that directs the operator to check the eluent, and said second information means provides a second guidance indication that directs the operator to check the check sample and the reagent.

16. A chemical separation and detection system according to claim 13, further comprising:

fourth storage means for storing a reference degree of separation range;

third identification means for comparing a degree of separation of the check sample and the reference degree of separation range when the predetermined number and the detected number of peaks in the check sample chromatogram are coincident; and third information means for informing the operator of a third guidance indication that directs the operator to exchange the separation column when the degree of separation of the check sample is out of the reference degree of separation range when the predetermined number and the detected number of peaks in the check sample chromatogram are coincident.

17. A chemical separation and detection system according to claim 13, further comprising:

further storage means for storing a reference ratio of quantities range of predetermined components;

further identification means for comparing the ratio of quantities of predetermined components a sample and the reference ratio of quantities range of predetermined components when the predetermined number and the detected number of peaks in the check sample chromatogram are coincident; and further information means for informing the operator of a further guidance indication that directs the operator to check the check sample and the reagent when the ratio of quantities of predetermined components is out of the reference ratio of quantities range of predetermined components when the predetermined number and the detected number of peaks in the check sample chromatogram are coincident.

18. A chemical separation and detection system according to claim 13, wherein said detection means comprises means for detecting a biochemical sample obtained from a living body.

19. A chemical separation and detection system according to claim 18, wherein said detection means comprises means for detecting a catecholamine or glycated hemoglobin.

20. A chromatograph system for analyzing a specific sample, comprising:

first storage means for storing a predetermined number indicative of a number of peaks of components to be detected;

second storage means for storing a reference retention time range;

analysis means for exclusively analyzing a predetermined check sample and a specific sample of interest to obtain chromatograms thereof;

means for comparing a number of peaks detected in the chromatograms of the check sample and the predetermined number, each detected peak being of a size greater than a predetermined lower-limit value;

means for inhibiting the specific sample of interest from being subjected to analysis by said analysis means and for informing an operator of a guidance indication that the check sample may be deteriorated when the predetermined number and the detected number of peaks in the check sample chromatogram are not coincident;

first identification means for comparing the retention time of a predetermined peak in the chromatogram of the predetermined check sample and the reference retention time range when the predetermined number and the detected number of peaks in the check sample chromatogram are coincident;

first information means for informing an operator of a first guidance indication regarding an eluent when the retention time of the predetermined peak is out of the reference retention time range when the predetermined number and the detected number of peaks in the check sample chromatogram are coincident;

third storage means for storing a reference peak size range;

second identification means for comparing the peak size of the predetermined peak and the reference peak size range when the predetermined number and the detected number of peaks in the check sample chromatogram are coincident; and second information means for informing the operator of a second guidance indication regarding the predetermined check sample being employed when the peak size of the predetermined peak is out of the reference peak size range when the predetermined number and the detected number of peaks in the check sample chromatogram are coincident.

21. A chromatograph system according to claim 20, further comprising:

means for automatically injecting an unknown sample into said analysis means when the retention time and the peak-size of the predetermined peak are both within the respective reference ranges;

further storage means for storing a reference peak size ratio range;

further identification means for comparing the peak size ratio of predetermined peaks in the chromatogram and the reference peak size ratio range when the peak size of the predetermined peak is within the reference peak size range; and further information means for informing the operator of a further guidance indication that directs the operator to check the predetermined check sample when the peak size ratio of the predetermined peaks is out of the reference peak size ratio range.

22. A chromatograph system for analyzing a specific sample, comprising:

first storage means for storing a reference retention time range;

analysis means for exclusively analyzing a predetermined check sample and the specific sample of interest to obtain chromatograms thereof;

first identification means for comparing the retention time of a predetermined peak in the chromatogram of said predetermined check sample and the reference retention time range when a predetermined number and the detected number of peaks in the check sample chromatogram are coincident;

first information means for informing an operator of a first guidance indication regarding an eluent when the retention time of the predetermined peak is out of the reference retention time range when the predetermined number and the detected number of peaks in the check sample chromatogram are coincident;

second storage means for storing a reference peak size range;

second identification means for comparing the peak size of the predetermined peak and the reference peak size range when the predetermined number and the detected number of peaks in the check sample chromatogram are coincident;

second information means for informing the operator of a second guidance indication regarding the predetermined check sample being employed when the peak size of the predetermined peak is out of the reference peak size range when the predetermined number and the detected number of peaks in the check sample chromatogram are coincident;

third storage means for storing the predetermined number, indicative of a number of peaks of components to be detected;

means for comparing a number of peaks detected in the chromatograms of the check sample and said predetermined number, each detected peak being of a size greater than a predetermined lower-limit value; and means for inhibiting the specific sample of interest from being subjected to analysis by the analysis means and for informing an operator of a guidance indication that the check sample may be deteriorated when the predetermined number and the detected number of peaks in the check sample chromatogram are not coincident;

further storage means for storing a reference peak size ratio range;

further identification means for comparing the peak size ratio of predetermined peaks in the chromatogram and the reference peak size ratio range when the peak size of the predetermined peak is within the reference peak size range when the predetermined number and the detected number of peaks in the check sample chromatogram are coincident; and further information means for informing the operator of a further guidance indication that directs the operator to check the predetermined check sample when the peak size ratio of the predetermined peaks is out of the reference peak size ratio range when the predetermined number and the detected number of peaks in the check sample chromatogram are coincident.

23. A chemical separation and detection system for analyzing a specific sample, comprising:

a separation column for separating a component of the sample, a detection means for detecting retention time, quantity and degree of separation of said component in the sample, first storage means for storing a reference retention time range for the component in a check sample, first identification means for comparing the reference retention time and a retention time of the component in the check sample when a predetermined number and the detected number of peaks in the check sample chromatogram are coincident, second storage means for storing a reference quantity of the component range in the check sample, second identification means for comparing the reference quantity of the component range and the quantity of the component in the check sample when the predetermined number and the detected number of peaks in the check sample chromatogram are coincident, first information means for informing an operator of a first guidance indication regarding an eluent when the retention time of the component in the check sample is out of the reference retention time range when the predetermined number and the detected number of peaks in the check sample chromatogram are coincident, second information means for informing the operator of a second guidance indication regarding the check sample being employed when the quantity of a component in the check sample is out of the reference quantity of the component range when the predetermined number and the detected number of peaks in the check sample chromatogram are coincident, third storage means for storing the predetermined number indicative of a number of peaks of components to be detected, analysis means for exclusively analyzing the check sample and the specific sample of interest to obtain chromatograms thereof, means for comparing a number of peaks detected in the chromatograms of the check sample and said predetermined number, each detected peak being of a size greater than a predetermined lower-limit value, and means for inhibiting the specific sample of interest from being subjected to analysis by the analysis means and for informing an operator of a guidance indication that the check sample may be deteriorated when the predetermined number and the detected number of peaks in the check sample chromatogram are not coincident.

24. A chemical separation and detection system according to claim 23, wherein said first information means provides a first guidance indication that directs the operator to check the eluent, and said second information means provides a second guidance indication that directs the operator to check the check sample.

25. A chemical separation and detection system according to claim 23, further comprising:

further storage means for storing a reference ratio of quantities range of predetermined components;

further identification means for comparing the ratio of quantities of predetermined components a sample and the reference ratio of quantities range of predetermined components when the predetermined number and the detected number of peaks in the check sample chromatogram are coincident; and further information means for informing the operator of a further guidance indication that directs the operator to check the check sample when the ratio of quantities of predetermined components is out of the reference ratio of quantities range of predetermined components when the predetermined number and the detected number of peaks in the check sample chromatogram are coincident.

* * * * *